United States Patent [19]

Blackman

[11] Patent Number: 5,098,717
[45] Date of Patent: * Mar. 24, 1992

[54] METHOD OF TREATMENT FOR PRURITUS

[75] Inventor: Steven T. Blackman, New York, N.Y.

[73] Assignee: Thames Pharmacal Co., Inc., Ronkonkoma, N.Y.

[*] Notice: The portion of the term of this patent subsequent to May 29, 2007 has been disclaimed.

[21] Appl. No.: 656,592

[22] Filed: Feb. 19, 1991

Related U.S. Application Data

[63] Continuation-in-part of Ser. No. 130,445, Dec. 9, 1987, Pat. No. 5,013,545.

[51] Int. Cl.$^5$ .................... A01N 25/04; A61K 31/78; A61K 9/70; A61K 47/12
[52] U.S. Cl. .................... 514/648; 424/405; 424/443; 424/445; 424/447; 424/484; 424/486; 424/487; 514/263; 514/264; 514/651; 514/724; 514/784; 514/785; 514/944; 514/969
[58] Field of Search ............... 424/81, 405, 443, 445, 424/447, 484, 486, 487; 514/263, 264, 651, 724, 944, 969, 784, 785

[56] References Cited

U.S. PATENT DOCUMENTS 4,166,177  8/1979  Cragoe, Jr. et al. ............... 514/825

FOREIGN PATENT DOCUMENTS 0068552  1/1983  European Pat. Off. .
1465665  2/1977  United Kingdom .
2017491 10/1979  United Kingdom .

Primary Examiner—Thurman K. Page
Assistant Examiner—Carlos Azpuru
Attorney, Agent, or Firm—Kirschstein, Ottinger, Israel & Schiffmiller

[57] ABSTRACT

A method of treating a pruritic skin area in a mammal by application to the affected area of a gel composition containing from about 60 to about 90% ethyl alcohol, from about 0.5 to about 30% water, at least one gelling agent and a pharmaceutically effective amount of a topically active, antipruritic, antihistaminic agent. The gel may be applied to the affected area from one to five times daily.

19 Claims, No Drawings

METHOD OF TREATMENT FOR PRURITUS

CROSS-REFERENCE TO RELATED APPLICATION

This application is a continuation-in-part of co-pending application Ser. No. 07/130,445, filed Dec. 9, 1987 now U.S. Pat. No. 5,013,545.

BACKGROUND OF THE INVENTION

1. Field of the Invention

The present invention relates to methods of treating pruritus.

2. Description of the Prior Art

Many pharmaceutical agents are available for the topical treatment of pruritus in humans and animals. Low to medium potency corticosteroids are often used to treat the inflammatory and pruritic manifestations of acute dermatitides. Topical antipruritics such as menthol, phenol and camphor and topical anesthetics (most commonly, benzocaine) are also frequently applied to relieve pruritus of the skin.

In the case of mast cell-mediated (particularly histamine-mediated) pruritic manifestations, topical antihistamines, e.g., diphenhydramine, are sometimes effective in relieving itch and erythema. These topical preparations conventionally take the form of creams and lotions, which provide relatively short-duration antipruritic activity and must be applied frequently to continue relief from itching.

SUMMARY OF THE INVENTION

It is an object of the present invention to provide a method of effectively relieving pruritus in mammals, for extended periods of time without requiring frequent applications of topical medication.

Another object of the present invention is to provide a method as aforesaid utilizing topical compositions which are safe and easy to apply and store.

Still a further object of the present invention is to provide methods as aforesaid utilizing gel formulations of topically active antihistamines.

In keeping with these objects and others that will become apparent hereinafter, the present invention resides, briefly stated, in a method of treating pruritus comprising the topical application of a gel containing from about 60 to about 90% by weight ethyl alcohol, from about 0.5 to about 30% by weight water, and from about 0.5 to about 5% of at least one gelling agent capable of gelling the alcohol-water system, together with a pharmaceutically effective amount of a topically active, antipruritic, antihistaminic agent. Preferred antihistamines include diphenhydramine and diphenhydramine hydrochloride.

The gel compositions used in the novel methods may optionally include gelling enhancers, gel neutralizing agents, ultraviolet absorbing agents, emollients, humectants, clarifiers and coloring and fragrance additives.

The compositions used in the present invention can be packaged in any standard containers known in the pharmaceutical and cosmetic arts to be suitable for storage and dispensing of gels for topical use, including any of a variety of tubes, bottles, pouches, and the like. The compositions are useful for the treatment of any topical pruritic condition known to be responsive to antihistamine therapy, including, by way of example, contact dermatitis, allergic dermatitis, urticaria, insect bites, mast cell disease and reactions to intradermal allergy testing.

DETAILED DESCRIPTION OF THE INVENTION

The aqueous topical gel compositions used in the methods of the present invention comprise from about 60% to about 90% by weight ethyl alcohol; from about 0.5% to about 30% by weight water, preferably purified or distilled; from about 0.5% to about 5% by weight of at least one gelling agent; and a pharmaceutically effective amount of a topically active, antipruritic, antihistaminic agent.

As used herein, a "pharmaceutically effective amount" of a topically active antihistaminic agent means a percentage concentration of that agent known in the medical and pharmaceutical arts to be safe and effective in treating dermatological conditions—e.g., from about 0.5 to about 3.5% diphenhydramine or diphenhydramine HCl, and preferably from about 1 to about 2.5%. Various concentrations of the same active ingredient may be used to provide for variations in the age of the patient to be treated, the severity of the condition and the duration of the treatment.

The gelling agents utilized in the subject compositions can be any agents which create a stable gel matrix in the presence of substantial quantities of alcohol and water. Preferred gelling agents for use in the present invention include the water-soluble, carboxyvinyl polymers known as carbomers or, by their commercial name, "CARBOPOLS" (B.F. Goodrich Chemical Co., Cleveland, Ohio). Carbomers are also alcohol-soluble but require neutralization for use in non-polar systems. A variety of effective neutralizing agents are known, including sodium hydroxide, potassium hydroxide and sodium bicarbonate, but preferred for the purposes of the present invention are polar organic amines such as triethanolamine and tetrahydroxypropyl ethylenediamine. Generally from about 0.2% to about 5% by weight of such neutralizing agents are sufficient to render the carbomer-created gels non-polar.

Optional ingredients in the gel compositions used in the novel methods include gelling enhancers, ultraviolet absorbers (to prevent degradation and discoloration of the gels), emollients and humectants. Suitable gelling enhancers include, by way of example, from about 0.1% to about 3% hydroxymethyl- and hydroxyethylcellulose.

Any of a variety of ultraviolet absorbers, emollients and humectants may be incorporated into the gels of the present invention to improve their stability, feel, and anti-drying properties when applied to the skin. Benzophenones are known ultraviolet absorbers which are effective in preventing gel degradation, particularly when a transparent or semi-transparent container is used. Effective emollients and humectants include, for example, lactate esters of fatty alcohols and glycerin.

In order to create a transparent gel, which may be preferable for esthetic reasons and for consumer acceptance, a gel clarifying agent may be added to the subject composition. An example of such agents which is highly effective in creating a transparent gel is "COSMEDIA" (Henkel, Ambler, Pa.), which is a polyacrylamidomethylpropane sulfonic acid.

It has been found that the preferred range of alcohol concentration for use in the gel compositions is from about 60 to about 80%, because formulations containing in excess of 80% alcohol, while suitable for the purposes of the invention, form less stable gels. Similarly, the preferred range of water concentrations is from about 8 to about 30% of the total composition.

Due to their high alcohol concentrations, the subject gels do not require any added preservatives.

The gels used in the present invention may be prepared by any conventional process known in the pharmaceutical and cosmetic arts. By one preferred procedure, the water (preferably in distilled or purified form) and all but 5-10% of the alcohol are combined with the primary gelling agent and agitated. Any gelling enhancers utilized are added to this phase.

A second phase is prepared by mixing the pharmaceutically effective amount of the active ingredient, generally from about 0.5% to about 5% of the total composition by weight, with the remaining alcohol. If necessary, the mixture may be carefully heated to 60° C. to assist in solubilizing the active ingredient. A small amount (0.05-1% by weight) of an ultraviolet absorber may optionally be added to this phase. The first and second phases are then rapidly mixed together until a homogeneous gel is obtained.

Humectants and emollients, comprising in total from about 1% to about 10% of the total weight of the composition, and a gelling agent neutralizer, comprising from about 1% to about 5% of the weight of the composition may also be mixed together to form another optional phase, which is preferably mixed into the first phase before addition of the phase containing the active ingredient. Coloring or fragrance additives may be mixed into the final gel product until suitable appearance and odor is obtained.

The gels used in the novel method, due to their high alcohol concentration and the presence of water, also act as good penetration enhancers for the incorporated antihistaminic ingredients by altering the stratum corneum and enhancing its permeability. This effect increases the potency of the topical agents which must penetrate below the outer skin surface in order to achieve good antipruritic activity.

The subject compositions are easy to package in conventional containers, tubes and pouches and have good stability upon long term storage at ambient temperatures. In such tubes, containers and pouches, the gels may be easily transported in an individual's pocket, purse or carrying bag and small quantities may be effectively dispensed for use with little waste and discomfort due to spillage. The compositions are also of pleasant appearance, odor and consistency, and are water washable and non-irritating, all of which promotes and enhances the patient's desire to use the compositions as needed and/or as prescribed by a physician.

The novel method of the present invention comprises the application of antihistamine-containing gels as described above to an affected skin area of a mammal to relieve pruritus. The gels are applied from 1 to about 5 times daily in sufficient quantities to cover the affected area, and provide a high degree of antipruritic activity for an extended period of time, up to six hours or more. By contrast, prior art antihistaminic creams and lotions provide relief of short duration and must be applied frequently.

The following examples provide detailed illustrations of formulations for the gel compositions used in the present invention as well as methods of treatment employing the same. These examples are not intended, however, to limit or restrict the scope of the invention in any way, and should not be construed as providing methods, conditions, ingredients or starting materials which must be utilized exclusively to practice the present invention.

EXAMPLE 1

Antihistaminic Gel

Five kilograms of an antihistaminic gel were prepared utilizing the following ingredients:

| Ingredient | Quantity | Percentage of Total (w/w) |
|---|---|---|
| Phase A | | |
| CARBOPOL 940 (carboxyvinyl polymer, B. F. Goodrich Chemical Co., Cleveland, Ohio) | 50.0 g | 1.0% |
| NATROSAL 250 HHF (hydroxyethyl cellulose, Hercules, Inc., Wilmington, Delaware) | 10.0 g | 0.2% |
| Alcohol USP | 2.75 kg | 55.0% |
| Purified Water | 1.32 kg | 26.3% |
| Phase B | | |
| CERAPHYL ($C_{12-15}$ alcohols lactate, Van Dyk & Co., Belleville, New Jersey) | 125.0 g | 2.5% |
| Glycerin | 125.0 g | 2.5% |
| QUADROL POLYOL (tetrahydroxypropyl ethylenediamine, BASF Wyandotte Corp.) | 135.0 g | 2.7% |
| Phase C | | |
| Menthol | 15.0 g | 2.7% |
| UVINUL MS-40 (benzophenone, BASF Wyandotte Corp., Parsippany, New Jersey) | 5.0 g | 0.1% |
| Diphenhydramine HCl | 100.0 g | 2.0% |
| Alcohol USP | 250.0 g | 5.0% |
| Phase D | | |
| FDC Blue #1 | 0.0125 g | .00025% |

The alcohol an purified water of Phase A were mixed in a steam-jacketed stainless steel kettle. The Carbopol 940 gelling agent and Natrosal 250 gelling enhancer were sprinkled into the alcohol/water mixture with rapid mixing.

The ingredients of Phase B were accurately weighed and then charged into a separate steam-jacketed stainless steel kettle where they were thoroughly mixed. Phase B was then added to Phase A with continued mixing to form a gel.

The ingredients of Phase C were subsequently mixed and added to the gel with continued agitation until homogeneous. Phase D was then added to the gel and mixing continued until uniform color and consistency were obtained.

EXAMPLES 2-3

Antihistaminic Gels

The procedure of Example 1 was repeated with the relative proportions of the ingredients changed as follows:

| Ingredients | Weight Percentages | |
|---|---|---|
| | Ex. 2 | Ex. 3 |
| CARBOPOL 940 | 1.25% | 1.5% |
| NATROSAL 250 HHF | 0.25% | 0.3% |
| Alcohol USP (Phase A) | 70.0% | 85.0% |
| Purified Water | 12.1% | 0.55% |
| CERAPHYL | 2.5% | .5% |
| Glycerin | 2.5% | 0.5% |
| QUARDOL POLYOL | 3.8% | 4.05% |

-continued

| Ingredients | Weight Percentages | |
|---|---|---|
| | Ex. 2 | Ex. 3 |
| Menthol | 0.5% | 0.5% |
| UVINUL MS-40 | 0.1% | 0.1% |
| Diphenhydramine HCl | 2.0% | 2.0% |
| Alcohol USP (Phase C) | 5.0% | 5.0% |

EXAMPLE 4

Method of Treatment for Pruritus

A human patient suffering from a histamine-mediated, pruritic skin eruption is treated by applying a sufficient amount of a gel according to Example 1 to cover the affected area with a thin film. The gel is applied from one to five times daily, as needed.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims.

I claim:

1. A method of treating pruritus in an affected skin area of a mammal comprising the application to the skin area of a gel composition including:
   (a) from about 60 to about 90% by weight ethyl alcohol;
   (b) from about 0.5 to about 30% by weight water;
   (c) from about 0.5 to about 5% by weight of at least one gelling agent; and
   (d) a pharmaceutically effective amount of a topically active, antipruritic, antihistaminic agent.

2. A method according to claim 1 wherein said antihistaminic agent is diphenhydramine or diphenhydramine hydrochloride.

3. A method according to claim 2 wherein said antihistaminic agent is diphenhydramine hydrochloride.

4. A method according to claim 1 wherein said composition includes from about 60 to about 80% alcohol by weight.

5. A method according to claim 1 wherein said composition includes from about 8 to about 30% water by weight.

6. A method according to claim 1 wherein said gelling agent is a carboxyvinyl polymer.

7. A method according to claim 1 wherein said composition additionally includes from about 0.2 to about 5% of a gel neutralizing agent by weight.

8. A method according to claim 7 wherein said gel neutralizing agent is selected from the group consisting of triethanolamine and tetrahydroxypropyl ethylenediamine.

9. A method according to claim 1 wherein said composition additionally includes from about 0.1 to about 3% gelling enhancer by weight.

10. A method according to claim 9 wherein said gelling enhancer is selected from the group consisting of hydroxymethyl cellulose and hydroxyethylcellulose.

11. A method according to claim 1 wherein said composition additionally includes an ultraviolet absorbing ingredient.

12. A method according to claim 1 wherein said composition additionally includes an emollient or humectant ingredient.

13. A method according to claim 1 wherein said composition additionally includes a gel clarifying ingredient.

14. A method according to claim 3 wherein said composition additionally includes about 0.5 to about 3.5% diphenhydramine hydrochloride by weight.

15. A method according to claim 14 wherein said composition additionally includes about 1 to about 2.5% diphenhydramine hydrochloride by weight.

16. A method according to claim 15 wherein said composition includes about 2% diphenhydramine hydrochloride by weight.

17. A method according to claim 4 wherein said composition includes about 60% ethyl alcohol.

18. A method according to claim 4 wherein said composition includes about 75% ethyl alcohol.

19. A method according to claim 1 wherein said composition is applied to the skin area from 1 to about 5 times daily.

* * * * *